United States Patent [19]

Wilson

[11] Plant 4,916

[45] Nov. 2, 1982

[54] PEACH TREE

[75] Inventor: William J. Wilson, Fort Valley, Ga.

[73] Assignee: Bountiful Ridge Nurseries, Inc., Princess Anne, Md.

[21] Appl. No.: 236,693

[22] Filed: Feb. 23, 1981

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Frank B. Robb

[57] ABSTRACT

A peach tree designated "Clyde Wilson" having leaves of dark green upper surface, yellowish green under surface, flowers of pink color overall, fruit appearance of yellowish red with reddish areas, flesh which appears to be yellow overall, the cavity being reddish in general, a particularly valuable characteristic for commercial production being the fact that the ripening period in effect extends the season of the "Loring" (Unpatented) variety since the fruit is similar and sizes well when a heavy crop is produced.

1 Drawing Figure

The present invention relates to a new and distinct variety of peach tree which I have designated as W-850 and which will be known commercially as "Clyde Wilson" variety.

My new variety was discovered by me as a sport of "Loring", an unpatented variety growing in my cultivated orchard at Ft. Valley, Ga.

It was discovered as a sport of "Loring" because the sport limb carried green fruit even when the last tree of the "Loring" variety had been picked for the last time. Since the fruit did remain it was observed to determine whether it would ripen and have potential as an attractive commercial variety.

After repeated asexual reproduction by budding and continued observation, it has been determined that the characteristics come true and the aspect of late ripening is particularly valuable, inasmuch as the effect is to extend the picking season since the fruit is enough like the parent "Loring" to provide an excellent commercial variety. In fact the volume of fruit produced is quite comparable to the old established Elberta variety and thus even more important commercially.

The period by which the season is in effect extended, varies somewhat but is at least seven days and often fourteen days.

Since the color of the fruit is an attractive overall red with yellow background, it compares favorably with the parent "Loring" and it is particularly important to note that the fruit sizes well, even when the tree is carrying a heavy crop.

Further the volume of fruit per tree has been established as very good and thus growers will find it to be an important addition to their usual varieties.

The fact that the characteristics set forth are consistently maintained when trees are grown at Ft. Valley, Ga. in my cultivated orchard and also near Princess Anne, Md. under cultivated conditions, is important to support wide spread planting and production from a commercial operation in which substantial numbers of trees may be involved.

In describing certain specific aspects of the tree and fruit, it is notable that the leaves are a dark green upper side and yellowish-green beneath.

The flowers are an attractive pink and the overall fruit color may best be described as yellowish-red with darker reddish areas.

The flesh generally appears overall to be yellow with decided reddish color near the cavity.

More specific aspects and details of my new variety are set forth in the appended description referring to the same and disclosed in the drawing wherein the leaves and fruit, both overall and sectioned are in color as nearly true as it is reasonably possible to make the same in a color illustration of this character, which shows shape of those elements as well.

The limitations imposed by color photography are found in these illustrations as would be expected, and may thus be slightly different from true colors though undoubtedly much of the fruit will be like the disclosure herein.

In the detailed description of my new variety of peach tree, the color terminology is that related to the Munsell Color Cascade published by MacBeth Division of Kollmorgen Corporation, except where color terms of ordinary dictionary significance are suitable.

Parentage: A sport of the variety "Loring" (unpatented).

Locality where grown and observed: Near Fort Valley, Ga. and Princess Anne, Md.

Dates of first and last pickings: August 16 to August 28.

Tree: Large size; vigorous; spreading; tall; vase formed; rapid growing; hardy; very productive; regular bearer.

*Trunk.*—Medium; smooth.

*Branches.*—Medium thickness and smoothness. Color — Red.

*Leaves.*—Length — $6\frac{3}{8}$ inches. Width — $1\frac{5}{8}$ inches. Form — Ovate; taper pointed; thick. Color — Dark green (16-15) upper side. Greenish yellow (23-12) under side. Margin — Finely serrate. Petiole — Short — $\frac{1}{4}$ inch. Thickness — Medium.

Flowers: Dates of first and full bloom — April 6 to April 10. Size — Large. Color — Pink (45-2) overall appearance.

Fruit:

*Maturity when described.*—Mid August.

*Size.*—Uniform. Axial diameter — About $2\frac{7}{8}$ inches. Transverse diameter — About 3 inches.

*Form.*—Uniform; symmetrical; regular; globose; ribbed.

*Cavity.*—Unsymmetrical. Depth — ½ inch. Breadth — About ⅞ inches.

*Stem.*—Clubbed; stout. Length — ¼ inch.

*Skin.*—Tough; smooth. Ground color — Golden (27-8). Color markings — Mottled; blushed. Bloom — Abundant. General color effect — Yellowish red (33-6) with reddish areas.

Flesh: Juicy.

*Color.*—Yellowish (28-6) overall.

*Texture.*—Firm; melting.

*Flavor.*—Delicate; aroma pronounced.

*Quality.*—Good.

Use: Market; local; dessert.

Keeping quality: Medium; about three weeks in ordinary storage conditions.

Resistance to disease: Good; to bacterial spot and non-browning.

I claim:

1. A new and distinct variety of peach tree of the yellow fleshed type, substantially as herein shown and described, characterized particularly as to novelty by the unique combination of late ripening of a fruit quite similar to the "Loring" (Unpatented) variety, extending the season on the order of seven to fourteen days, the excellent sizing of the fruit even where the tree is carrying a heavy crop, the attractive fruit having overall yellowish red appearance with substantial areas of red, the flesh being of yellowish appearance overall, distinctly reddish cavity and further the ability to produce fruit on a comparable basis in widely spaced geographic areas.

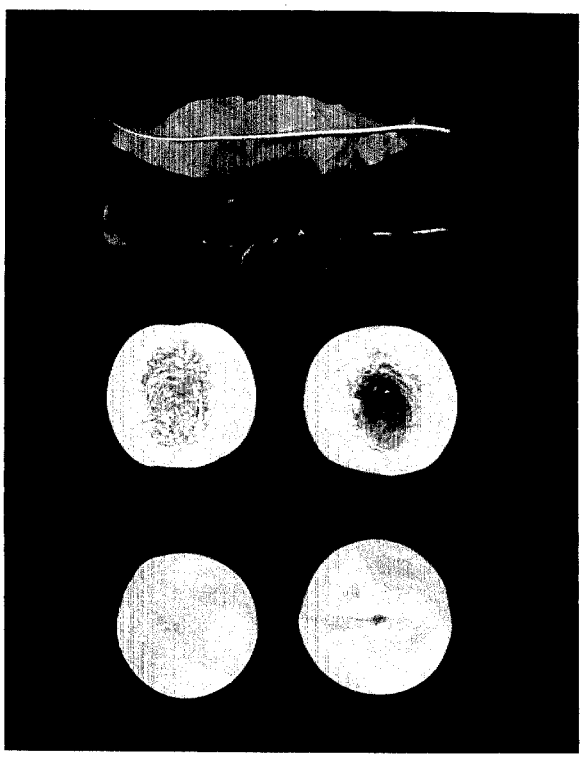

* * * * *